United States Patent [19]

Bianco

[11] Patent Number: 5,366,967
[45] Date of Patent: Nov. 22, 1994

[54] POTENTIATION OF THE ANTI-REACTIVE-ANTIASTHMATIC EFFECT OF INHALED LOOP DIURETICS BY INHALED NON-STEROIDAL ANTI-INFLAMMATORY DRUGS

[75] Inventor: Sebastiano Bianco, Milan, Italy
[73] Assignee: Hoechst Aktiengesellschaft, Frankfurt am Main, Germany
[21] Appl. No.: 65,450
[22] Filed: May 21, 1993

Related U.S. Application Data

[63] Continuation of Ser. No. 832,165, Feb. 6, 1992, abandoned.

[30] Foreign Application Priority Data

Feb. 9, 1991 [EP] European Pat. Off. ........ 91101817.4

[51] Int. Cl.$^5$ .................... A61K 31/60; A61K 31/62; A61K 31/615; A61K 31/16
[52] U.S. Cl. .................................. 514/59; 514/161; 514/162; 514/166; 514/613
[58] Field of Search ................ 514/159, 161, 162, 166, 514/613

[56] References Cited

U.S. PATENT DOCUMENTS 4,888,343  12/1989  Jones ................................... 514/264
4,908,382  3/1990  Bianco ................................. 514/471

FOREIGN PATENT DOCUMENTS 0386700  9/1990  European Pat. Off. ... A61K 31/635

OTHER PUBLICATIONS

Merck Manual, 14th ed. pp. 626–627 1982.
Chem. Abst. 92-87818u (1980).
Chem. Abst. 98-191520A (1983).
Chem. Abst. 101-83581T (1984).
S. Bianco et al., "Protective Effect of Inhaled Furosemide on Allergen–Induced Early and Late Asthmatic Reactions," N. Eng. J. Med., vol. 321, No. 16, (1989), pp. 1069–1073.
M. Rubuschi et al., "Inhaled Frusemide is Highly Effective in Preventing Ultrasonically Nebulised Water Bronchoconstriction," Pulmonary Pharmacology, vol. 1, (1989), pp. 187–191.
*Dorland's Illustrated Medical Dictionary*, 26th ed. (Philadelphia, W.B. Saunders Co., 1981), p. 399.
P. Sestini, *Am. Rev. Resp. Dis.*, vol. 145, No. 4, 1992, p. A728.
I. H. Wilkens, *Am. rev. Resp. Dis.*, vol. 143, No. 4, 1991, p. A458.
S. Bianco, *Progress in Biochem. Pharmacol.*, vol. 20, 1985, pp. 132–142.
A. J. Fairfax, *Prostaglandins Leukotrienes and Medicine*, vol. 8, No. 3, 1982, pp. 239–248.

*Primary Examiner*—Gregory Hook
*Attorney, Agent, or Firm*—Finnegan, Henderson Farabow, Garrett & Dunner

[57] ABSTRACT

The antireactive-antiasthmatic effect of inhaled loop diuretics is potentiated by the use of a combination of a loop diuretic and a non-steroidal anti-inflammatory drug as an inhalant for combating asthma. The use of a cyclooxygenase inhibitor as the non-steroidal anti-inflammatory drug is preferred, particularly preferred is the use of furosemide as the loop diuretic. Especially advantageous is the use of piretanide as the loop diuretic. Particularly preferred is the use of acetylsalicylic acid as the non-steroidal anti-inflammatory drug.

The most remarkable finding of this invention is the excellent and steady protective effect afforded by the combination of the two drugs in the patients with late asthmatic reactions between the seventh and eighth hour, when the effect of treatment with either drug alone appeared to be progressively decreasing.

2 Claims, 7 Drawing Sheets

POTENTIATION OF THE ANTI-REACTIVE-ANTIASTHMATIC EFFECT OF INHALED LOOP DIURETICS BY INHALED NON-STEROIDAL ANTI-INFLAMMATORY DRUGS

This application is a continuation, of application Ser. No. 07/832,165, filed Feb. 6, 1992, now abandoned.

The invention relates to the potentiation of the antireactive-antiasthmatic effect of inhaled loop diuretics by inhaled non-steroidal anti-inflammatory drugs.

Despite the fact that more refined drugs are available and that asthma care is better overall, nevertheless the mortality and morbidity of asthma appear to be increasing. In the 1970's great attention was paid to bronchospasm—contraction of bronchial smooth muscle—and its undoubted role in airflow limitation. Selective beta2-agonists came to the forefront of therapy, and the therapeutic benefits were derived. In the 1980's when a knowledge of basic mechanisms in asthma had improved significantly, the role of airways inflammation was introduced and emphasized. Until then, even in symptomatic asthmatics, widespread background inflammatory changes were present which were poorly controlled, if at all, by beta2-agonist drugs.

This knowledge served to put the spotlight on anti-inflammatory drugs such as corticosteroids and more recently on some non-steroidal anti-inflammatory drugs (NSAIDs) like cromoglycate and nedocromil sodium. Corticosteroids, however, are not specific and are known to be responsible for hypopituitary-adrenal (HPA) axis suppression at higher doses. Furthermore, their effect on exercise-induced asthma is indirect and unhelpful at times. Thus, non-steroidal anti-inflammatory drugs for treatment of asthma have obtained increasing importance.

Additionally, the inhalation of these drugs, resulting in an significant lowering of the administered dose and avoidance of systemic absorption, is known.

It is also known that high doses of oral acetylsalicylic acid (ASA), but not the chemically related sodium salicylate, and other NSAIDs show an antireactive activity by inhibition of the cyclooxygenase activity. The afforded protective effect is a result of the subsequent inhibition of the prostaglandin production which plays a relevant role in the bronchial response to certain bronchoconstrictor stimuli.

Recently, the loop diuretic furosemide has also been found to be an effective antireactive agent when it is administered by inhalation in ultrasonically nebulized water (UNW) -, exercise- and allergen-induced asthma (Pulmonary Pharmacology 1989, 1:187–191; N. Engl. J. Med. 1989, 321:1069–1073).

The interaction of NSAIDs with the diuretic effects of furosemide are well documented.

However, until now there has been no indication suggesting that NSAIDs might influence the asthmatic effects of loop diuretics.

The invention set out to determine the specific interactions of NSAIDs with loop diuretics which could possibly lead to a reduction of the doses of the loop diuretic while retaining the efficacy in the treatment of asthma.

The aim of this invention was to potentiate the antireactive-antiasthmatic effect of inhaled loop diuretics. This was accomplished by the use of a combination of a loop diuretic and a non-steroidal anti-inflammatory drug as an inhalant for combating asthma. The use of a cyclooxygenase inhibitor as the non-steroidal antiinflammatory drug is preferred, particularly preferred is the use of furosemide as the loop diuretic. Especially advantageous is the use of piretanide as the loop diuretic. Particularly preferred is the use of acetylsalicylic acid as the non-steroidal antiinflammatory drug.

The present study was undertaken to investigate whether inhaled NSAIDs could influence the antireactive-antiasthmatic activity of loop diuretics, particularly of furosemide. Unexpectedly, it was found that pretreatment with inhaled ASA results in a strong potentiation of the antireactive activity of furosemide on both non-specific and specific bronchial stimuli.

PATIENTS AND METHODS

A) Studies on non-specific bronchial hyperreactivity

Patients: Patients were studied with either allergic or non-allergic asthma, clinically and functionally stable, with a baseline forced expiratory volume at one second (FEV,) greater than 70% of predicted and free of viral or bacterial respiratory infection for at least 4 weeks. None of the patients had a history of L-ASA induced asthma. All the patients received either no treatment or were treated with inhaled beta2-stimulants and topical steroids, that were withheld 10 hours before the test (Chay H., J Allergy Clin Immunol 1975; 56:323–327).

Methods

Bronchial reactivity to ultrasonically nebulized water was measured as previously described ( Pulmonary Pharmacology 1989, 1:187–191).

Each subject inhaled increasing doubling doses of distilled water mist produced by an ultrasonic nebulizer (DeVilbiss Ultraneb 99) set to an output of 2 ml/min. The subjects were instructed to breath at tidal volume, keeping the mouthpiece between their teeth and with the mouth semi-opened. Doubling doses of UNW were administered by progressively increasing the time of exposure from 30" (1 ml) to 240" (15 ml) and if necessary for further 240" doubling amounts by increasing the output was increased to 4 ml/min (31 ml). The respiratory function was monitored after each dose until a $FEV_1$ decrease of between 15 and 20% or more compared with baseline was observed. In the cases where specific airway resistance (sRaw) was measured, this was done during normal breathing using a constant-volume body plethysmograph with a closed bag system to condition air to body temperature pressure saturation (BTPS) (Fenyves & Gut, Basel, Switzerland) before and after pretreatment, and immediately after each test. $FEV_1$ was measured using a spirometer (Vitalograph). The best value from the first 3 technically satisfactory spirograms was chosen for analysis. The dose of UNW causing a 15% or 20% $FEV_1$ decrease ($PD_{15}$ and $PD_{20}$) was then calculated by interpolation on the cumulative dose-response curve.

Study design

To study the effect of inhaled NSAIDs on the antireactive activity of inhaled furosemide against UNW-induced bronchoconstriction, we firstly investigated the effect of L-ASA in a group of 7 patients with a positive response to UNW in a preliminary challenge (table I), in a single blind, cross-over study compared to placebo using a random-number table for randomization. Each patient performed four UNW bronchial challenges within an interval of 2 to 7 days. Before each test, the patients received an aerosol of either L-ASA 90 mg/ml in saline, corresponding to 50 mg/ml of acetyl salicylic acid (Flectadol ®, Maggioni-Winthrop S.p.A., Milan, Italy) or placebo (normal saline) for 10 minutes, given by means of a jet nebulizer (Soffio, Markos, Monza, Italy) set to an output of 0.18 ml/min, followed by a second aerosol of furosemide 10 mg/ml (Lasix ®, Hoechst) or placebo for an additional 10 minutes. The UNW test was then performed as previously described.

To test the effect of a cyclooxygenase inhibitor other than L-ASA, in a pilot study, the experiment was conducted in two more patients according to the same protocol except that indomethacin 5 mg/ml was given by inhalation instead of L-ASA.

Additionally, in four more patients, the effects of indomethacin and furosemide were determined according to the same protocol used for the previous studies except that in this study 3 ml of a 5 mg/ml solution of indomethacin were administered and the UNW PD20 and UNW PD15 were determined.

B) Studies on allergen-induced reactions

Patients

Volunteers with allergic asthma who had an early obstructive response after specific allergen bronchial challenge were recruited from patients attending an allergy clinic. All the patients had a clinical history of allergic asthma and/or rhinitis and a positive immediate skin reaction to the clinically relevant allergen. They were either asymptomatic or had very mild respiratory symptoms, had a baseline $FEV_1$ over 70% of predicted and had been free of respiratory infections for at least 4 weeks. The patients received either no treatment or occasional topical bronchodilator therapy, that was withheld at least 10 hours before the challenges. Patients sensitive to pollen were investigated outside the pollen season.

Methods

The specific bronchial challenge was performed as previously reported (N Engl. J Med 1989, 321:1069-1073). In a preliminary bronchial challenge, the allergen (Frazioni Alfa, Dome/Hollister-Stier, Bayropharm Italiana, Milano, Italy) was administered by a dosimeter (MEFAR, Bovezz. a, Italy). The apparatus was manually operated by the investigator and set for an aerosol delivery of 3.7 $\mu$l/puff in 0.6 seconds, with a pause of 6 seconds between the puffs. The allergen was dissolved in normal saline at a concentration of 40 Activity Units (AU) per ml for doses up to 2.4 AU (corresponding to a delivered dose of 0.15 AU/puff), of 160 AU/ml for doses up to 9.6 AU (0.6 AU/puff) and of 320 AU/ml (1.2 AU/puff) for higher doses. AU were determined by the manufacturer using the Radio Allergy Sorbant Test (RAST) inhibition assay compared with a reference preparation characterized by skin bioreactivity. $FEV_1$ and Peak Expiratory Flow Rate (PEFR) were measured using a dry spirometer (Vitalograph, Buckingham, England) and a mini-Wright Peak Flow Meter (Clement Clarke International Ltd., London, England) before and 10 minutes after administration of a first dose of 0.15 AU. The procedure was then repeated doubling the dose of allergen until a 25% or greater decrease of $FEV_1$ from baseline was observed, or a maximum allergen dose of 19.2 AU was reached. The provocative dose of allergen causing a 25% $FEV_1$ decrease ($PD_{25}$) was then calculated by interpolation from the cumulative dose-response curve, plotted on semilogarithmic paper. To verify the occurrence of a late asthmatic reaction, respiratory function was monitored every 60 minutes after challenge up to 8 hours either by spirometry or with a peak flow meter. A 15% or greater decrease of either measurement after 3 hours or more, compared with baseline, associated with symptoms of bronchial asthma, was considered as a bronchial late allergic response. A control measurement was also obtained at the same time points on a different day, without allergen exposure, and patients showing variations of 10% or more during the day were considered clinically unstable and excluded.

Study design

The effect of the combination of inhaled NSAID and furosemide on the bronchial responses to allergen challenge was investigated in two different studies.

In the first study, the effect of pre-treatment with L-ASA on the immediate bronchial allergic response was investigated in three subjects in a single blind, cross-over study compared to placebo, using a random-number table for randomization. Each patient performed four bronchial challenges within an interval of 4 to 14 days, using a single dose of allergen corresponding to the PD25 calculated in the preliminary challenge. Before each test, the patients received an aerosol with 4 ml of either L-ASA 9.0 mg/ml in saline, corresponding to 50 mg/ml of acetyl salicylic acid (Flectadol ®, Maggioni-Winthrop S.p.A., Milan, Italy) or a placebo ([normal saline) for 8 minutes, given by means of a jet nebulizer (Mod. Solrio, Markos, Monza, Italy) with an output of 0.27 ml/min, followed by a second aerosol containing 4 ml of furosemide 10 mg/ml (Lasix ®, Hoechst) or placebo for an additional 8 minutes. Immediately thereafter, the selected dose of allergen was delivered by a dosimeter. Specific airway resistance (sRaw) was measured during normal breathing using a constant-volume body plethysmograph with a closed bag system to condition air to BTPS (Fenyves & Gut, Basel, Switzerland) before and after pretreatment and at 5, 10, 15, 20, 30, 45 and 60 minutes after challenge. These measurements were made at least in quintuplicate and the mean was computed. $FEV_1$ was obtained by integration of flows measured with a No. 3 Fleisch pneumotacograph connected to the body plethysmograph. The best value from the first 3 technically satisfactory spirograms was chosen for analysis.

To investigate the effect of pre-treatment with inhaled L-ASA on the late phase of the asthmatic reaction, five additional patients (table II) were also studied who presented a dual asthmatic response to the preliminary challenge, characterized by the occurrence of a second obstructive response after the resolution of the immediate response, between the fourth and the eighth hour after challenge. The study was conducted according to the previous protocol (New Engl J of Med, 1989, 321:1069-1073), except that the time of nebulization of the drugs was increased to 15', the post-test methacholine challenge was not performed, and the respiratory function parameters were monitored every 60 minutes for eight hours post-challenge.

Data analysis

Data were expressed as absolute values or as a percentage of baseline values at time zero, i.e. after pretreatment and immediately before allergen challenge.

Changes of UNW reactivity were measured as doubling doses of UNW $PD_{20}$ compared to placebo, and calculated as $\log_2$ (PD$_{20}$ after drug)—$\log_2$(PD$_{20}$ after placebo). An increase of the PD$_{20}$ by one doubling dose then corresponds to a 100% increase of the cumulative dose of nebulized water causing a 20% FEV$_1$ decrease compared to baseline. The same analysis was used for PD$_{15}$.

The percentage protective effects for FEV$_1$ and for sRaw were calculated for each patient according to the formula:

((AUC placebo—AUC L-ASA)/AUC placebo)×100, where AUC is the area under the time-response curve of the absolute differences from baseline. All data were calculated without knowledge of the randomized treatment.

The two-way analysis of variance and the paired Student's t test were used for statistical comparison of normally distributed variables, and the method of the least-significant difference was used for multiple comparisons (see Shedecor G. W., Cochran W. G. Statistical methods. 7th ed. Ames, Iowa University Press, 1980). A level of $p<0.05$ (two-tailed) was considered significant.

RESULTS

Figure 1:
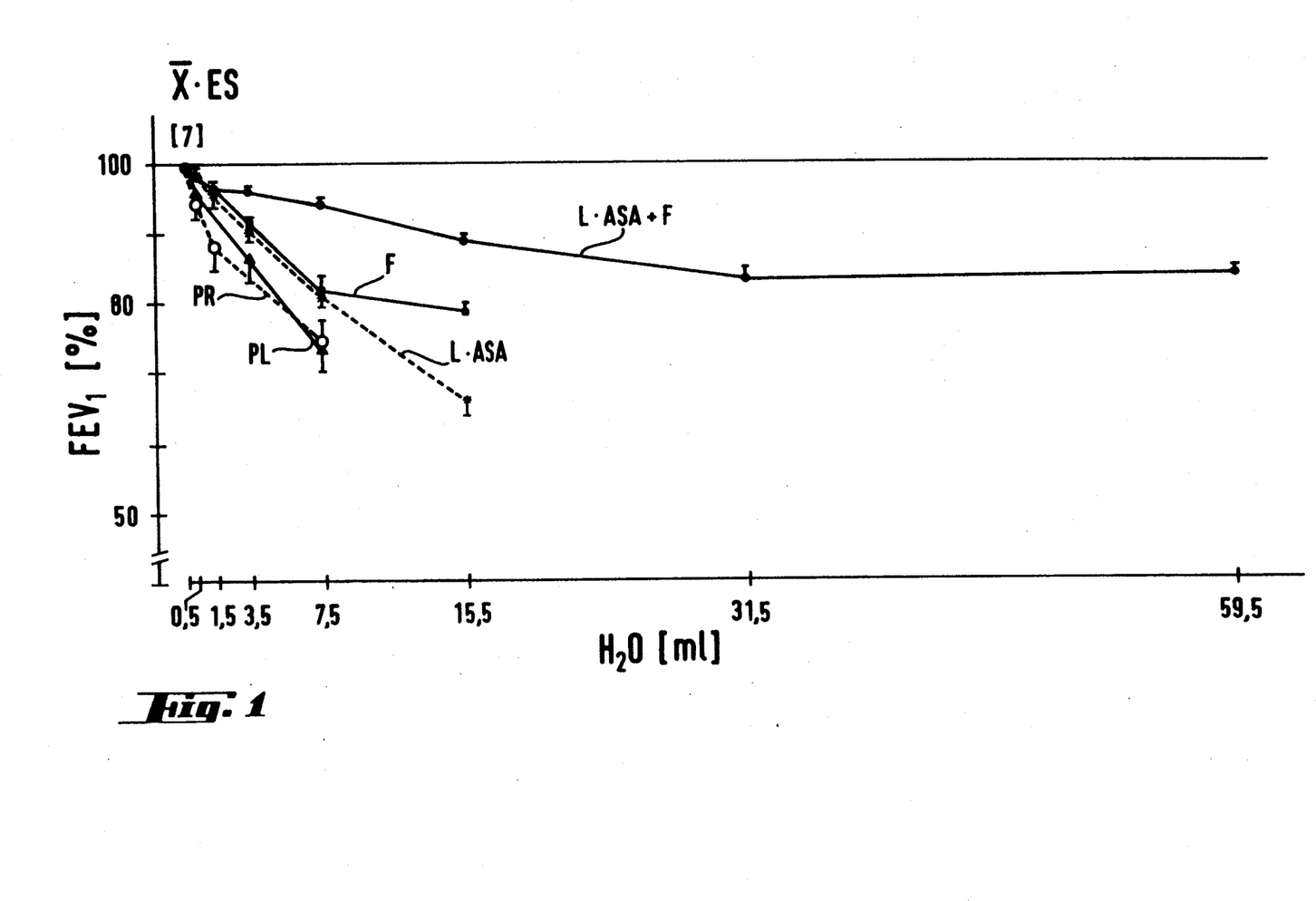
FIG. 1. Mean $FEV_1$ decrease compared to baseline at different doses of UNW of distilled water after different treatments in a group of 7 patients with asthma. PR: preliminary test; PL: placebo; F: inhaled furosemide; L-ASA: inhaled lysine monoacetylsalicylate; L-ASA+F: inhaled lysine monoacetylsalicylate+furosemide.

All the treatments under study were well tolerated by the patients, and no significant changes of respiratory function parameters were observed after drug inhalation. After treatment with placebo, the bronchial response to UNW was similar to the one observed in the preliminary test. Pretreatment with either inhaled L-ASA or furosemide caused a significant shift to the right in the dose-response curve (FIG. 1). However, combined treatment with L-ASA and furosemide caused a striking decrease of UNW reactivity, such that most of the subjects failed to reach a 20% FEV, decrease even at the highest dose of nebulized water. For this reason, results of this group were analyzed using the dose causing a 15% FEV$_1$ decrease (PD$_{15}$) rather than the PD$_{20}$.

Figure 2:
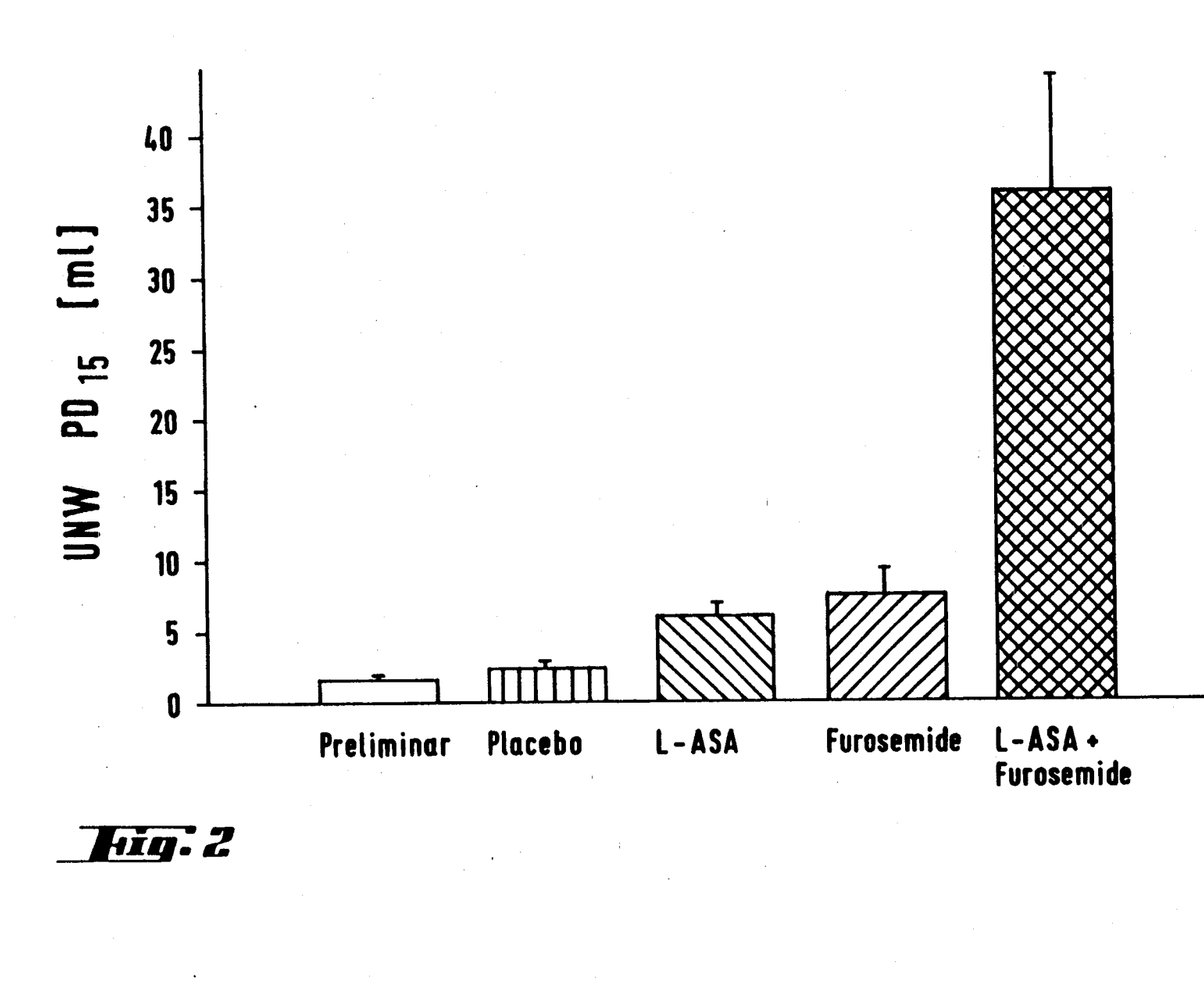
FIG. 2. Mean $PD_{15}$ to UNW after aerosol treatment with L-ASA and furosemide alone and in combination. Bar represent M±SE.

The synergistic effect of inhaled furosemide and L-ASA is well evident also in FIG. 2, where the mean PD$_{15}$ obtained in the study group is presented. Treatment with either inhaled L-ASA or furosemide caused a PD$_{15}$ increase of 1.6±0.4 and 1.8±0.5 doubling doses of water compared to placebo, respectively. After combined treatment with both drugs however, UNW reactivity was increased by 4.0±0.4 doubling doses, which is considerably higher than the sum of the effects of the single drugs.

Figure 3:
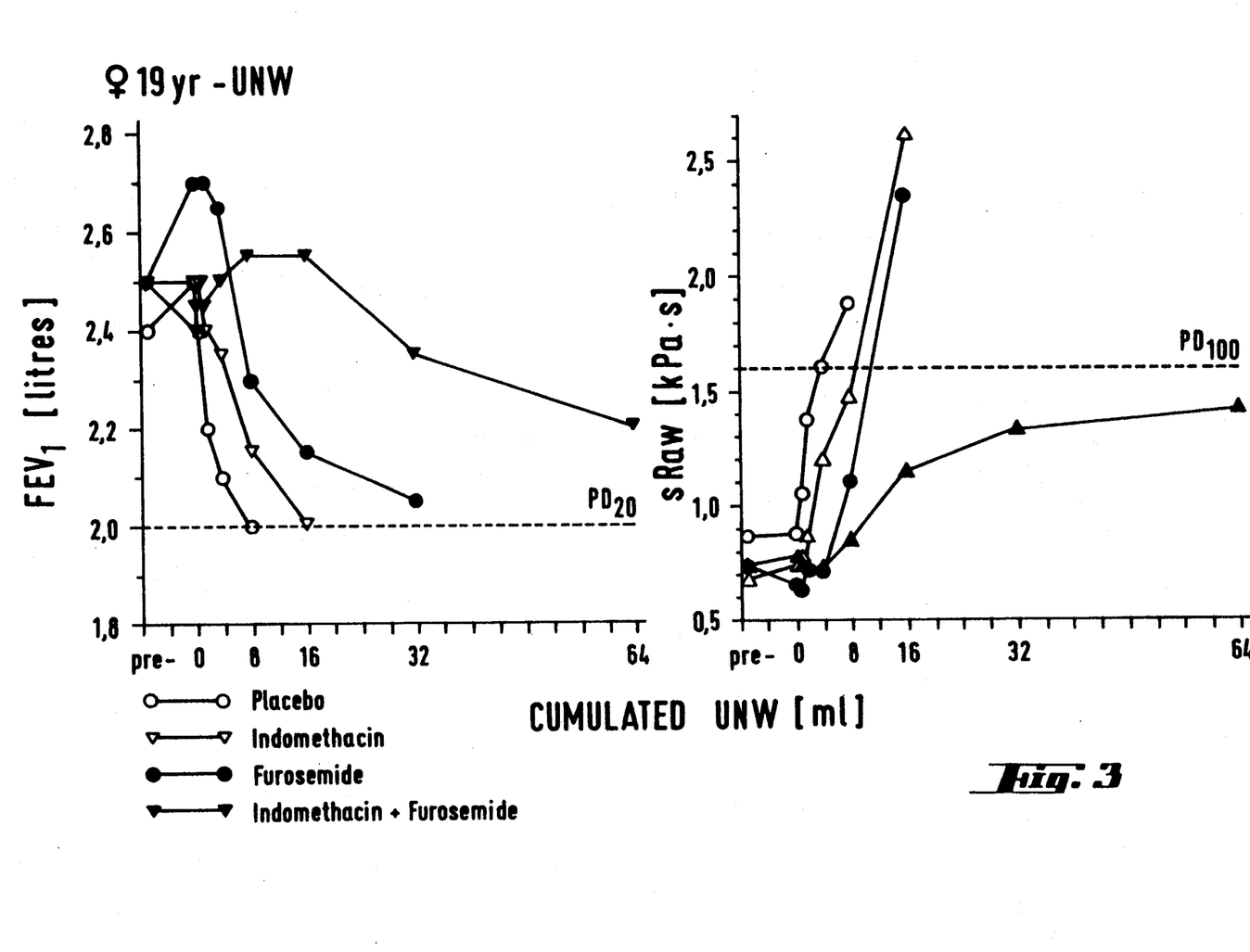
FIG. 3. Synergism of the antireactive effects of indomethacin and furosemide on the bronchial response to UNW measured as changes of $FEV_1$ (left) and sRaw (right). One case is presented of two tested with similar results.

A similar result was obtained in the pilot study in the two cases where indomethacin was used in place of L-ASA, one of which is shown in FIG. 3. The results of the four patients receiving 3 ml of a 5 mg/ml solution of indomethacin and furosemide are shown in tables IV and V. Table IV shows the patients' characteristics as well as the UNW PD20 values for four patients treated with either placebo, Indomethacin, Furosemide and Furosemide+Indomethacin according to the previous protocol.

Table V shows the respective data for PD 15 of the same patients.

Figure 4:
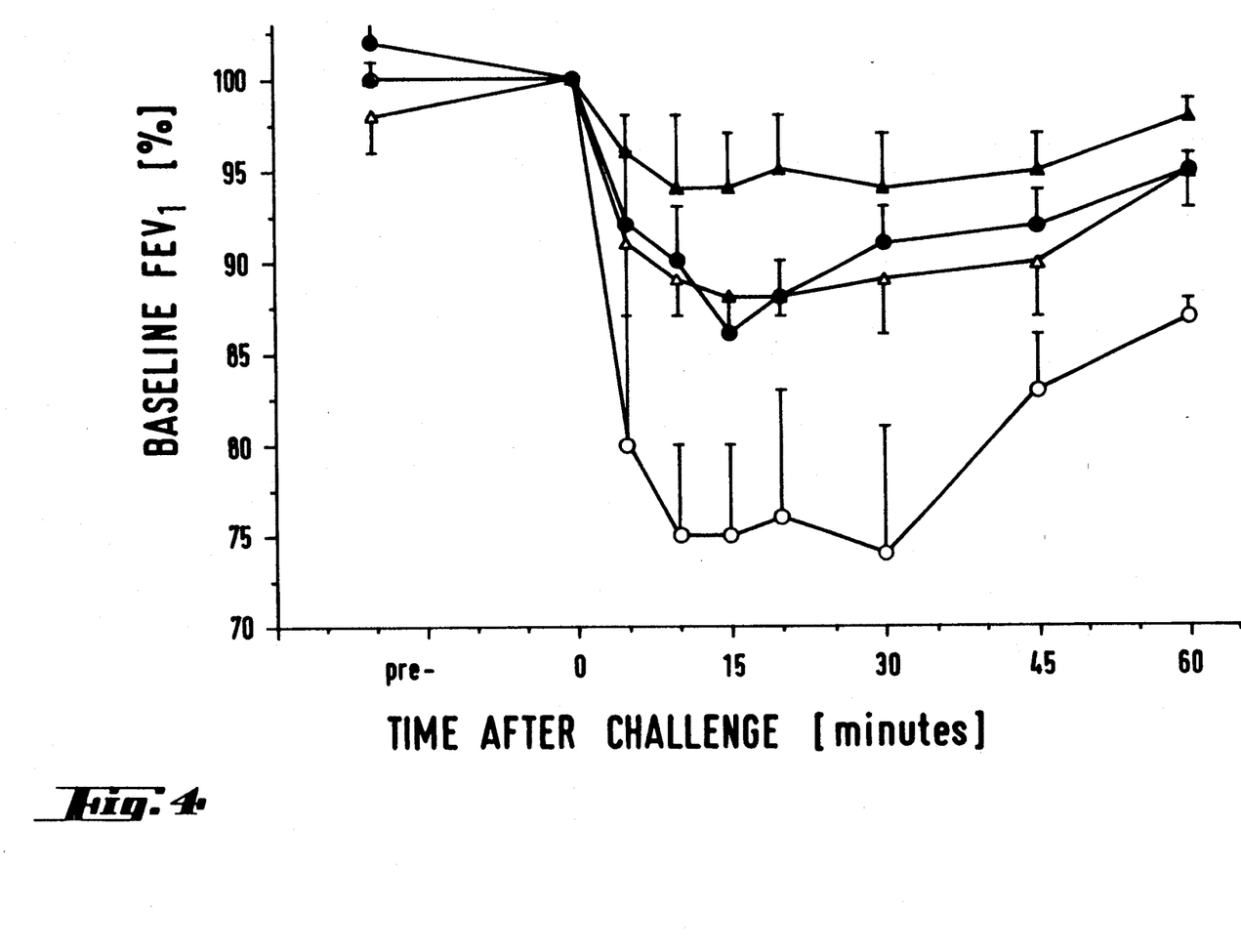
FIG. 4. Potentiating effect of inhaled L-ASA on the protective effect of inhaled furosemide against the early asthmatic response in 3 subjects, presented as M±SE of the percentage changes of $FEV_1$ compared to post-treatment baseline (see graph 6 for key). Baseline $FEV_1$ was 90±2% of predicted. Open circles: placebo, filled circles: furosemide, open triangles: L-ASA, filled triangles: L-ASA+furosemide.
Figure 5:
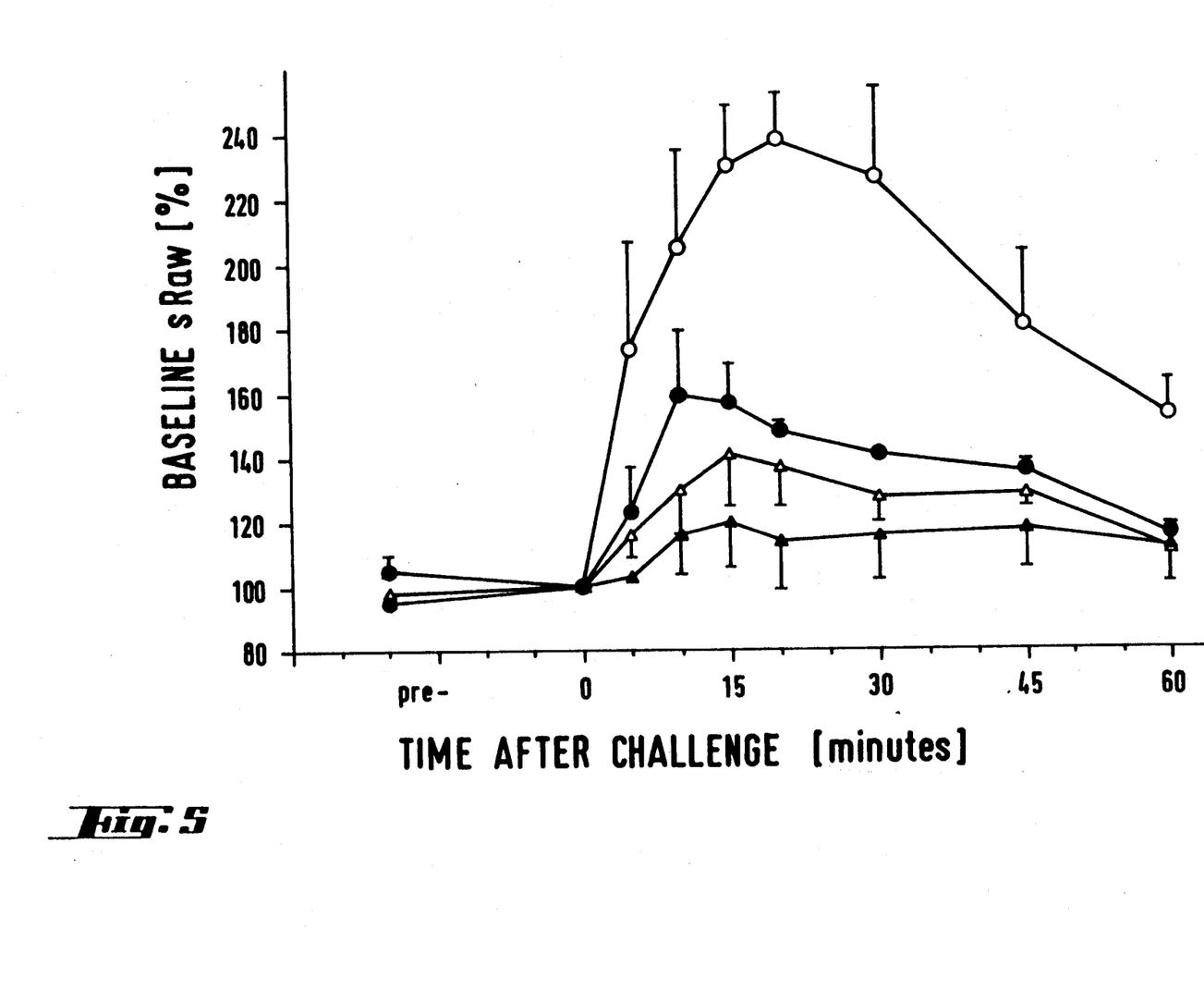
FIG. 5. Potentiating effect of inhaled L-ASA on the protective effect of inhaled furosemide against the early asthmatic response in 3 subjects, presented as M±SE of the percentage changes of sRaw compared to post-treatment baseline. (see graph 6 for key).

The effect of inhaled L-ASA and furosemide on the early asthmatic response in 3 patients, measured as changes of FEV$_1$ and sRaw, is presented in FIGS. 4 and 5, respectively. Also in this case the response after placebo was not different from the preliminary test, and treatment with furosemide or L-ASA caused a partial protection, whereas the combination of the two treatments almost completely blunted the reaction. The percentage protection compared to placebo after treatment with L-ASA, furosemide, and the combination of both was 58±1; 43±18 and 82±7% respectively for of FEV$_1$ and 53±13; 69±8 and 91±7% for sRaw.

Figure 6:
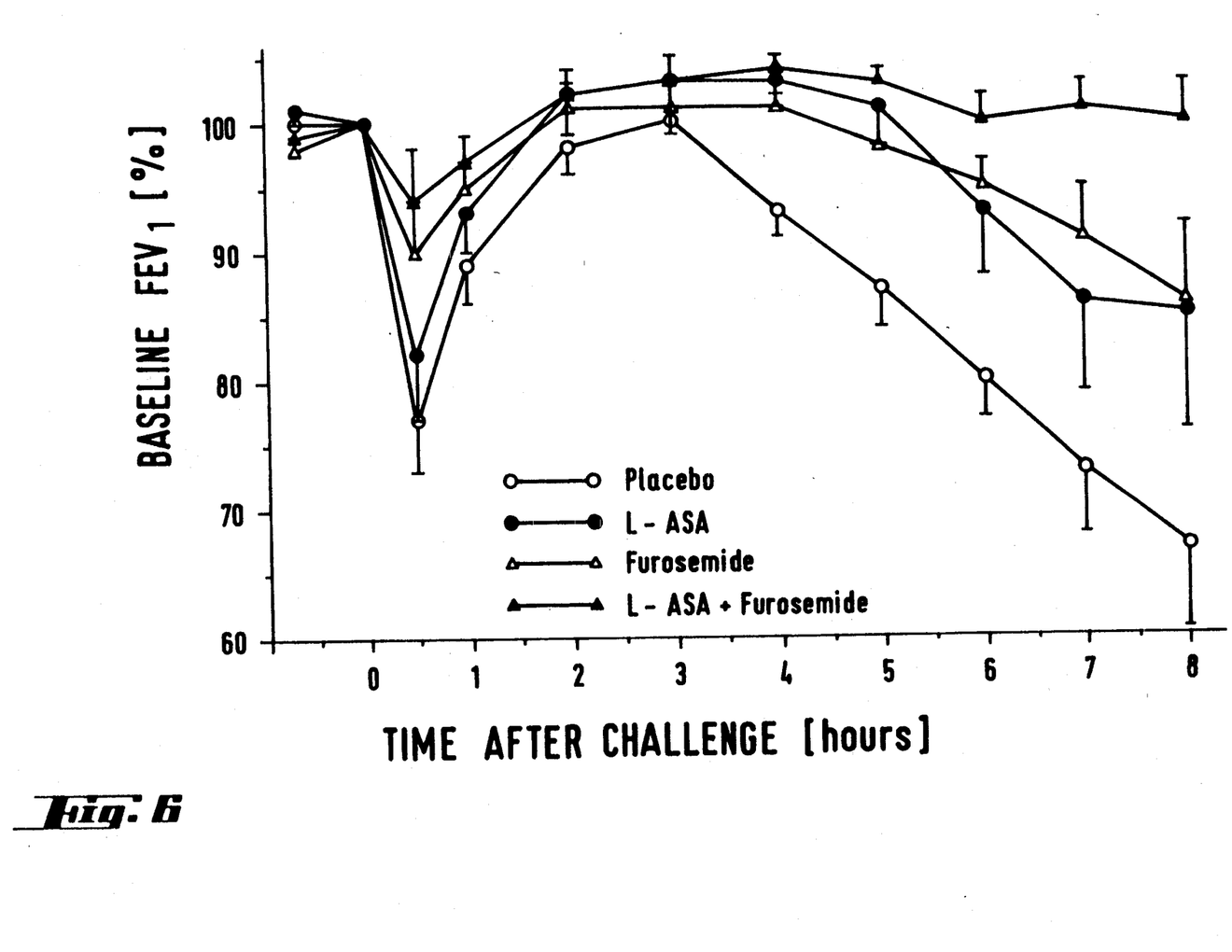
FIG. 6. Potentiating effect of inhaled L-ASA on the protective effect of inhaled furosemide against the early and late asthmatic responses in 5 subjects, presented as M±SE of the percentage changes of FEV, compared to post-treatment baseline. Baseline FEV, was 92±3% of predicted.
Figure 7:
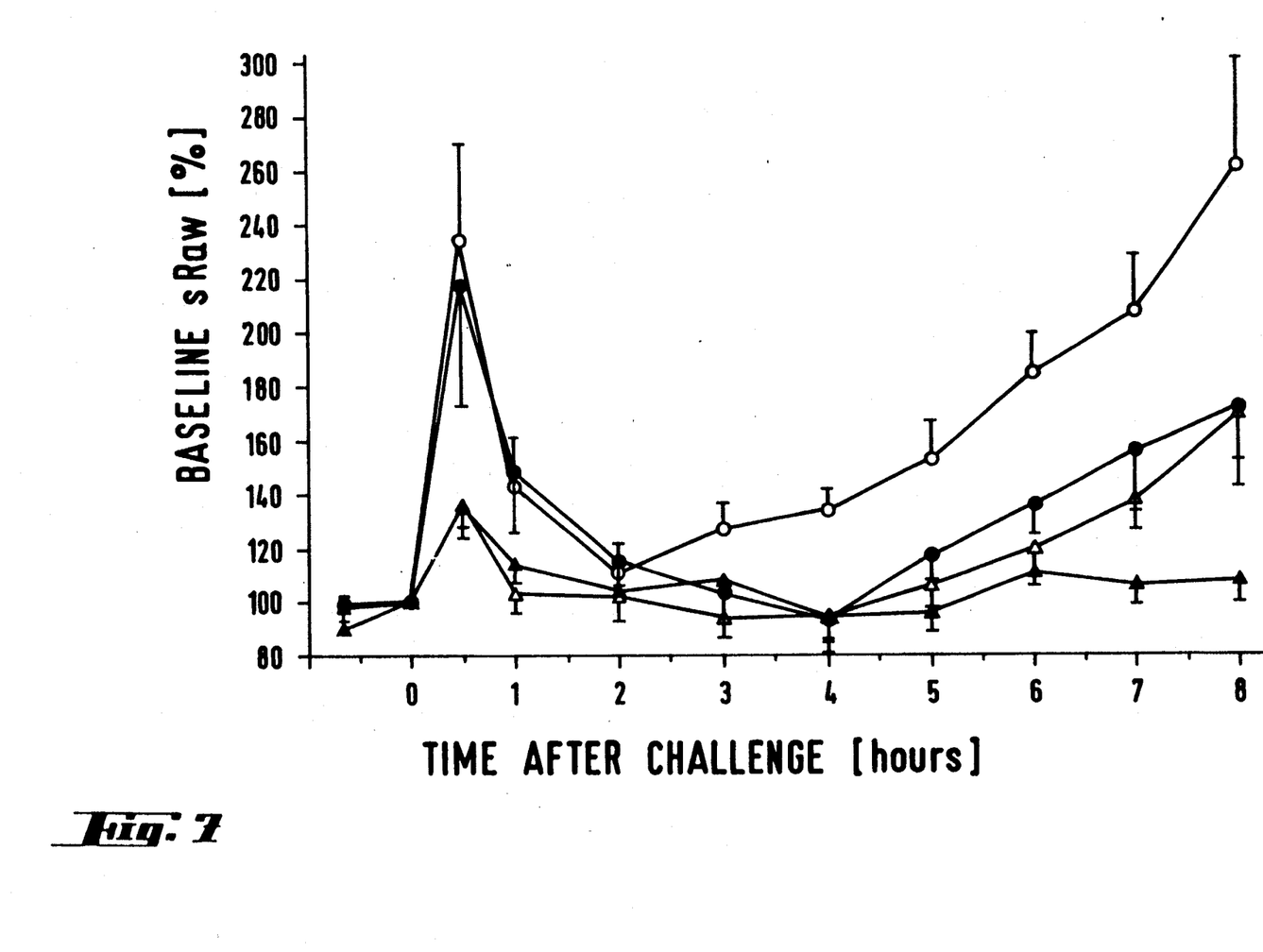
FIG. 7. Potentiating effect of inhaled L-ASA on the protective effect of inhaled furosemide against the early and late asthmatic responses in 5 subjects, presented as M±SE of the percentage changes of sRaw compared to post-treatment baseline (see graph 6 for key).

Inhaled treatment with L-ASA and furosemide was very well tolerated also in the group with late asthmatic reactions, and no changes of baseline respiratory function parameters were observed between the different study days or after any of the treatments (Table III). Inhalation of L-ASA had a limited effect on the early asthmatic reaction in this group of very sensitive individuals, compared to furosemide or compared with that observed in the previous group. However, the late asthmatic response was significantly protected by both treatments. More remarkably, treatment with both drugs in combination completely blunted both the immediate and the late reaction, as measured by FEV$_1$ (FIG. 6) and sRaw (FIG. 7). Mean percentage protection compared to placebo from time 0 to 8 hours after treatment with L-ASA, furosemide and the combination of both was 49±23; 85±18, and 109±11% respectively for FEV$_1$ and 35±20; 71±14 and 83±6% for sRaw.

DISCUSSION

These data clearly show that inhaled NSAIDs effectively potentiate the antireactive effect of inhaled furosemide against non-specific and specific stimuli. This potentiating effect is particularly impressive in the experiments with UNW, where only a dose related low effect was obtained with the single drugs compared to the combination of both, but it is also present in the early and late responses to allergen, indicating a potential therapeutic value for this combination. There is general agreement that the immediate obstructive reaction constitutes only an initial event of the bronchial allergic response, and it is now recognized that the late asthmatic reaction, which follows the immediate response in approximately 50% of patients, is more closely related to the basic pathogenetic mechanisms operating in bronchial allergic asthma. The late response shows clinical features and the therapeutic responses more akin to clinical asthma, and is more difficult to control compared to the early reaction (Am Rev Respir Dis 1977, 116:573-588, and Am Rev Respir Dis 1987; 136:740-51).

In fact, probably the most remarkable finding of this invention is the excellent and steady protective effect afforded by the combination of the two drugs in the patients with late asthmatic reactions between the seventh and eighth hour, when the effect of treatment with either drug alone appeared to be progressively decreasing.

The potentiating effect of NSAIDs on the antireactive activity of furosemide was unexpected, especially if the antagonistic effect observed between the two drugs on renal function is considered.

The data clearly indicate that the potentiating antireactive effect of NSAIDs and furosemide given by inhalation can be used to develop a new therapeutic strategy for the control of functional bronchial hyperreactivity and clinical asthma.

TABLE I

Effect of inhaled L-ASA on the antireactive activity of furosemide against UNW-induced bronchial reactions. Patients under study.

| N. | Sex | Age | $FEV_1$ liter | $FEV_1$ % pred | ALLERGY[a] | THERAPY[b] |
|---|---|---|---|---|---|---|
| 1 | F | 28 | 3.10 | 106 | GR | B2 |
| 2 | M | 47 | 2.77 | 81 | — | B2 ± CS |
| 3 | M | 22 | 3.75 | 94 | GR | B2 ± CS |
| 4 | M | 41 | 3.52 | 88 | — | B2 ± CS |
| 5 | M | 34 | 3.56 | 86 | DP | B2 ± CS |
| 6 | F | 39 | 2.19 | 87 | — | B2 ± CS |
| 7 | F | 47 | 2.01 | 82 | GR | B2 ± CS |

[a]DP: Dermatophagoides, GR: Grass pollen
[b]B2: inhaled beta2-agonist, CS: inhaled steroids

TABLE II

Effect of inhaled L-ASA on the protective effect of inhaled furosemide against allergen-induced late asthmatic reaction. Patients under study.

| N. | Sex | Age | $FEV_1$ liter | $FEV_1$ % pred | ALLERGY[a] $PD_{25}$ | ALLERGY[a] (AU) | THERAPY[b] B2 |
|---|---|---|---|---|---|---|---|
| 1 | F | 15 | 2.95 | 85 | DP | 1.0 | |
| 2 | F | 24 | 3.10 | 92 | PA | 0.8 | B2 |
| 3 | M | 20 | 4.85 | 98 | GR | 3.0 | B2 |
| 4 | F | 22 | 2.65 | 99 | DP | 0.2 | B2 |
| 5 | M | 18 | 2.75 | 82 | GR | 0.6 | B2 |

[a]GR: Grass pollen; PA: Parietaria Pollen; DP: Dermatophagoides
[b]B2: inhaled beta2-agonist

TABLE III

Baseline respiratory function parameters before and after treatment in the late asthmatic reaction study

| Treatment | $FEV_1$ (liters) BEFORE | $FEV_1$ (liters) AFTER | sRaw (kPa · sec) BEFORE | sRaw (kPa · sec) AFTER |
|---|---|---|---|---|
| placebo + placebo | 3.19 ± 0.34 | 3.18 ± 0.37 | 0.48 ± 0.03 | 0.50 ± 0.06 |
| L-ASA + placebo | 3.14 ± 0.36 | 3.09 ± 0.34 | 0.54 ± 0.04 | 0.55 ± 0.05 |
| placebo + furosemide | 3.12 ± 0.34 | 3.18 ± 0.32 | 0.48 ± 0.04 | 0.50 ± 0.04 |
| L-ASA + furosemide | 3.20 ± 0.33 | 3.22 ± 0.34 | 0.46 ± 0.04 | 0.52 ± 0.06 |

TABLE IV

Potentiation of the antireactive effect of Furosemide by inhaled Indomethacin (15 mg) UNW PD20

| No. | Sex | Age | FEV 1 % pred. | Atopy | Therapy | Prelim. | Placebo | Indom. | Furosem. | Furos. + Indom. |
|---|---|---|---|---|---|---|---|---|---|---|
| 1 | F | 21 | 88 | DP | B2 | 7.0 | 14.3 | 12.9 | 17.8 | 78.4 |
| 2 | F | 35 | 76 | PA | B2 CS | 5.6 | 6.0 | 19.4 | 21.5 | 32.3 |
| 3 | F | 38 | 74 | = | B2 CS | 6.7 | 10.6 | 28.9 | 6.6 | 43 |
| 4 | F | 15 | 68 | DP | B2 CS | 1.6 | 7.5 | 15.5 | 7.8 | 90.7 |
| Mean | | 27 | 77 | | | 5.2 | 9.6 | 19.2 | 13.4 | 61.1 |
| SE | | 6 | 4 | | | 1.2 | 1.8 | 3.5 | 3.7 | 13.9 | a) GR: Grass pollen; PA: Parietaria Pollen; DP: Dermatophagoides
b) B2: inhaled beta2-agonist, CS: inhaled steroids

TABLE V

Potentiation of the antireactive effect of Furosemide by inhaled Indomethacine (15 mg) UNW PD15

| No. | Sex | Age | FEV 1 % | Atopy | Therapy | Prelim. | Placebo | Indom. | Furosem. | Furos. + Indom |
|---|---|---|---|---|---|---|---|---|---|---|
| 1 | F | 21 | 88 | DP | B2 | 5.0 | 11.8 | 9.4 | 14.7 | 53.4 |
| 2 | F | 35 | 76 | PA | B2 CS | 4.7 | 4.7 | 12.9 | 16.7 | 22.2 |
| 3 | F | 38 | 74 | = | B2 CS | 3.8 | 8.4 | 16.0 | 4.4 | 34.0 |
| 4 | F | 15 | 68 | DP | B2 CS | 0.5 | 3.0 | 8.8 | 15.0 | 26.2 |
| Mean | | 27 | 77 | | | 3.5 | 7.0 | 11.8 | 12.7 | 34.0 |

TABLE V-continued

Potentiation of the antireactive effect of Furosemide by inhaled Indomethacine (15 mg) UNW PD15

| No. | Sex | Age | FEV 1 % | Ato py | The- rapy | Pre- lim. | Pla- cebo | In- dom. | Furo sem. | Furos. + Indom |
|-----|-----|-----|---------|--------|-----------|-----------|-----------|----------|-----------|----------------|
| SE  |     | 6   | 4       |        |           | ·1.0      | 2.0       | 1.7      | 2.8       | 6.9            | a) GR: Grass pollen; PA: Parietaria Pollen; DP: Dermatophagoides
b) B2: inhaled beta2-agonist, CS: inhaled steroids

I claim:

1. A method of treating asthma, which comprises administering by inhalation to a host in need thereof a combination of furosemide and acetylsalicylic acid in an amount effective to treat asthma.

2. A method of treating asthma, which comprises administering by inhalation to a host in need thereof a combination of furosemide and lysine monoacetylsalicylate in an amount effective to treat asthma.

* * * * *